United States Patent
Kyle et al.

[11] Patent Number: 6,018,389
[45] Date of Patent: Jan. 25, 2000

[54] CONE PENETROMETER FIBER OPTIC RAMAN SPECTROSCOPY PROBE ASSEMBLY

[75] Inventors: Kevin R. Kyle, Brentwood; Steven B. Brown, Livermore, both of Calif.

[73] Assignee: The Regents of the University of California, Oakland, Calif.

[21] Appl. No.: 08/898,713

[22] Filed: Jul. 22, 1997

Related U.S. Application Data

[63] Continuation-in-part of application No. 60/022,053, Jul. 22, 1996.

[51] Int. Cl.⁷ .......................................................... G01J 3/44
[52] U.S. Cl. ............................................................. 356/301
[58] Field of Search ...................... 356/301, 36, 318–319, 356/440, 410, 417; 250/253–270, 269.1–269.8, 269, 458.1, 459.1, 461.1, 461.2

[56] References Cited

U.S. PATENT DOCUMENTS

| | | |
|---|---|---|
| 2,632,801 | 3/1953 | Donaldson . |
| 5,112,127 | 5/1992 | Carrabba et al. ........................ 356/301 |
| 5,153,887 | 10/1992 | Krapchev . |
| 5,241,368 | 8/1993 | Ponstingl et al. . |
| 5,377,004 | 12/1994 | Owen et al. ............................. 356/301 |
| 5,491,344 | 2/1996 | Kenny et al. ......................... 250/461.1 |
| 5,561,516 | 10/1996 | Noble et al. . |

*Primary Examiner*—K. P. Hantis
*Attorney, Agent, or Firm*—John P. Wooldridge

[57] ABSTRACT

A chemically and mechanically robust optical Raman spectroscopy probe assembly that can be incorporated in a cone penetrometer (CPT) for subsurface deployment. This assembly consists of an optical Raman probe and a penetrometer compatible optical probe housing. The probe is intended for in-situ chemical analysis of chemical constituents in the surrounding environment. The probe is optically linked via fiber optics to the light source and the detection system at the surface. A built-in broadband light source provides a strobe method for direct measurement of sample optical density. A mechanically stable sapphire window is sealed directly into the side-wall of the housing using a metallic, chemically resistant, hermetic seal design. This window permits transmission of the interrogation light beam and the resultant signal. The spectroscopy probe assembly is capable of accepting Raman, Laser induced Fluorescence, reflectance, and other optical probes with collimated output for CPT deployment.

17 Claims, 7 Drawing Sheets

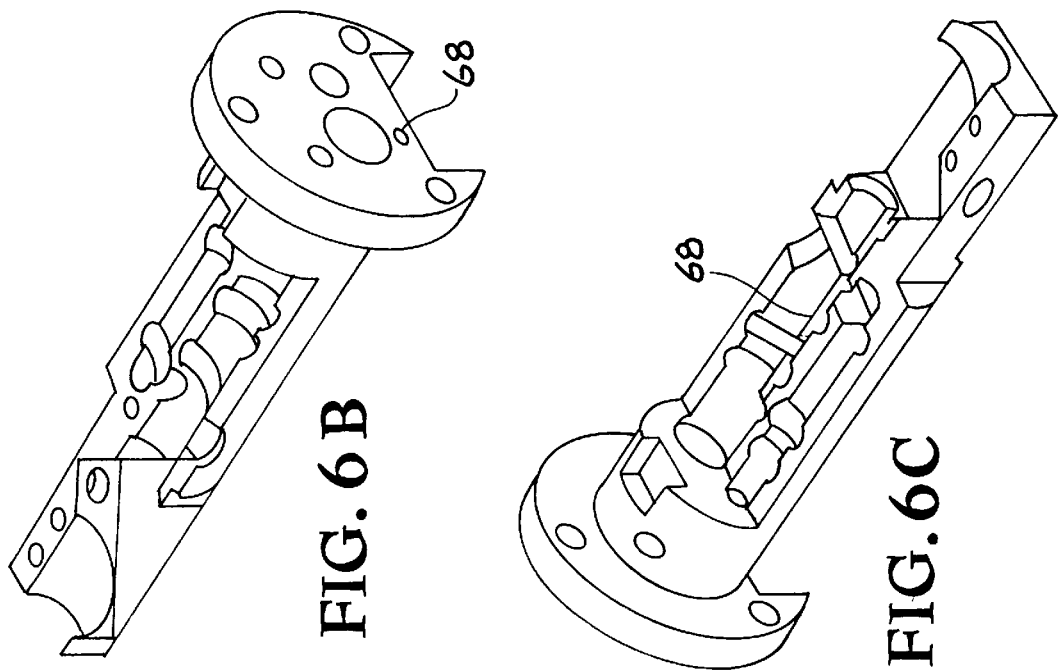
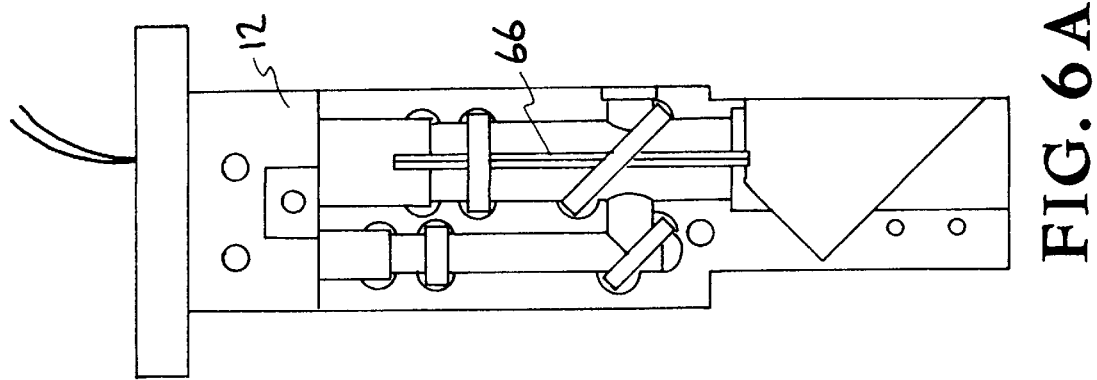

CONE PENETROMETER FIBER OPTIC RAMAN SPECTROSCOPY PROBE ASSEMBLY

This is a continuation-in-part of U.S. Provisional Patent Application Serial No. 60/022,053, titled: "Cone Penetrometer Fiber Optic Raman Spectroscopy Probe Assembly," filed Jul. 22, 1996.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to chemical characterization in harsh and chemically reactive environments, and more specifically, it relates to a specialized optical probe that provides spectral signals free from interfering signals found in currently available probes.

2. Description of Related Art

Induced radiative effects such as Raman scattering and fluorescence have become extremely valuable tools associated with the non-destructive determination of molecular constituents. To characterize a composition in a remote or hostile environment, optical fibers may advantageously be used to deliver excitation energy to a sample under investigation and to carry scattered radiation back to means for spectral analysis. An excitation source path may take the form of a laser providing a stimulus at an appropriate wavelength coupled to an input fiber, and a collection path may be made up of a second fiber carrying return radiative information to a spectral analysis tool such as a spectrograph.

Such remote spectral analysis presents technical challenges, however, including the strong scattering signature of the material used for the optical fiber, this interference potentially being generated by both the laser excitation in the illumination fiber and any strong Rayleigh (unshifted) Scattering allowed to enter the collection fiber. These spurious fiber signatures can compete with, or even overshadow, the desired signature of the sample under test, particularly when long lengths of fiber are used.

In U.S. Pat. No. 5,377,004, a narrowband reflective element not only folds the laser energy into a common sample illumination/collection optic, but also serves to reject a substantial portion of the Rayleigh scattering received from the sample. Since the reflection of a narrow band of wavelengths is much easier to control and improve than with transmission, this arrangement simultaneously reflects significantly more laser excitation light than a transmission element will pass, while transmitting more of the scattered signal than a transmission element will reflect, particularly those signals close to the excitation wavelength.

Additionally, folding of the illumination energy into an in-line collection path facilitates the use of a dispersive element, preferably another holographic optical element, in the illumination path to remove spurious scattering generated within the fiber from the excitation source. Such a highly efficient dispersive filtering element cannot be used in a configuration having the relatively weak spectra of interest folded out of an in-line illumination path. The use of a dispersive element also allows the use of spatial filters which may take advantage of apertures in the form of pinholes or slits in the illumination or sample path as a means to remove all but the laser energy.

A holographic notch filter may be inserted into the collection path between the narrowband reflective element and the return optical fiber, this notch filter being operative to further remove Rayleigh scatter from the scattered spectra. Additionally, beam redirection means may be provided so that the illumination and collection fibers may be substantially parallel to one another at their interface to the probe proper, thereby resulting in a more compact assembly. Preferably, a holographic transmission grating is utilized as this beam-redirecting device in the illumination path, thereby performing an additional function of excitation prefiltering before the primary filtering performed by the narrowband reflective element.

In other embodiments, a holographic beam splitter may be used as the means to redirect the illumination radiation, thus providing an alternative approach to laser light prefiltering. In further alternative embodiments, a holographic notch filter may be used as the narrowband reflective element, in which case the illumination path redirection means may take the form of another holographic notch filter or a holographic transmission or reflection grating. Mirrors or prisms may also be used advantageously in the illumination path, depending upon the desired final geometry.

In order to observe a process flow as opposed to direct sample illumination, a light-conductive element may be added between the probe and the environment under characterization, be it liquid, gaseous, plasma, etc. Preferably, this element is composed of a material which does not produce an unwanted signature, for example a nonsilica material such as fluorite.

U.S. Pat. No. 5,112,127 describes a fiber-optic probe which is useful for measuring Raman spectra of samples remote from the light source and detector. The probe head contains optical components which selectively remove unwanted fluorescence and Raman scattering arising from the interaction between the Raman excitation source radiation and the input optical fiber. The optics also filter the Raman excitation source into a return optical fiber leading to a spectrometer or detector. In one embodiment, the disposition of optical components provides a compact probe geometry with parallel input and output fibers at one end and a sampling port at the other end. An encasement for the optics is also disclosed, for sealing the components against the environment, and for coupling the probe to specialized sampling attachments, such as for conducting Surface Enhanced Raman Spectroscopy.

The probe is used as a component in instrumentation comprising 1) a light source, such as a laser which is coupled to an optical fiber or fiber bundle for the low-loss transmission of the light to the probe, which is placed in contact with the sample to be measured, and 2) a return fiber or fiber bundle exiting the probe which returns the light scattered from the sample to a spectroscopic analyzing instrument such as a spectrometer. The probe disclosed in this invention consists of 1) optics for filtering the excitation light, thus removing interfering Raman scattering and fluorescence arising from the excitation fiber; 2) optics for focusing the excitation light onto a sample external from the probe; 3) optics for collecting the scattered light from the sample and removing the intense laser excitation line from the desired spectral features; 4) optics for refocusing the scattered light for acceptance by the exit fiber or fiber bundle. An enclosure, ideally sealed from the environment, containing the optical components, is also a feature of the invention.

SUMMARY OF THE INVENTION

It is an object of the present invention to provide a fiber optic Raman probe for inclusion in a cone penetrometer.

The fiber optic Raman probe of the present invention is designed for collimated, colinear laser excitation and signal collection. The colinear probe provides maximal overlap of the interrogated area with the collection area and its inherently compact design facilitates emplacement in the limited space of the cone penetrometer. The probe sits within the cone penetrometer Raman probe interface along the penetrometer vertical axis. The penetrometer Raman probe interface is screwed directly into the penetrometer pipe, making it an integral portion of the penetrometer itself.

Optical communication between the vertically seated Raman probe and the sample environment along the radial axis of the penetrometer interface is accomplished, in one embodiment, with a gimbal mounted mirror, which is common to both the optical axis of the probe with the optical axis of the probe interface window train. The window train is terminated with an indium alloy hermetically sealed sapphire window which is designed to provide 1) optical access to the sample environment, 2) a chemically resistive surface that is flush with the penetrometer pipe exterior surface, and 3) structural integrity under at least 45 tons of vertical push force. Laser input to the probe is provided by a single fiber optic cable.

Collection of signal is performed, in one embodiment, by a seven fiber optic bundle. Seven collection fibers are used rather than one to increase the collection area and therefore efficiency of the probe, to allow for a larger laser spot size (4 mm) to be used when interrogating the sample, to decrease susceptibility to misalignment, and to reduce the bend radius relative to a single fiber of comparable diameter. A larger spot size results in increased signal to noise due to the larger area of coverage of the sample by minimizing the effect of inhomogeneous grain size. The collection fibers are filtered with a long pass filter to remove scattered laser light; the laser excitation fiber is filtered with a laser band pass filter to remove silica Raman generated in the optical fiber. This design provides complete rejection of silica Raman and both reflected and Rayleigh scattered laser line without compromising real signal. The probe is designed to provide complete rejection of silica Raman when the target utilized is a totally reflective polished flat surface.

The Raman Probe includes removable fiber optics which may be remotely disconnected and has a built-in compatibility with any commercially available or custom fiber connector. The probe includes built in beam dumps for complete elimination of silica Raman signal from excitation fiber. The light tight optical beam paths prevent cross talk or mixing of excitation and signal light. Built-in line and band pass filters provide laser line and signal selection. The large diameter collection channel allows high throughput of desired signal. Channels are provided for in situ optical calibrations at different wavelengths with broadband light source to give sample optical density information to normalize Raman signal intensity for sample absorbance of laser and scattered Raman signal. This removes the dependence of returned Raman signal on the color and/or light transmitivity of a sample. Built in optical alignment ports provide increased accuracy of optical alignment and ease of alignment. Interchangable side and end viewing capability is enabled by a removable gimbal mounted mirror for turning a beam from the vertical to the radial penetrometer optical axis. This allows a simple change from the radial viewing probe to the end viewing probe configuration with either a collimated or focused beam.

BRIEF DESCRIPTION OF THE DRAWINGS

FIGS. 6A–C show a fiber optic channel and fiber optic for broadband sample illumination.

DETAILED DESCRIPTION OF THE INVENTION

Chemically harsh environments are challenging due to the combination of strong oxidants (e.g., nitrates and/or nitrites), high caustic content, heat, and ionizing radiation (gamma, alpha). Prior art designs cannot withstand such a deployment environment or the push force required for cone penetrometer deployment. The present invention is a cone penetrometer fiber optic Raman probe assembly. A fiber optic Raman probe is inserted into a probe housing that is designed with a chemically inert, hermetic, metallic window seal to withstand chemical degradation. The window itself is chemically resistant and mechanically strong, capable of withstanding a push of up to 45 tons. The housing material consists of hardened stainless steel, utilized for both the mechanical strength and chemical resistance of the part.

Figure 1A:
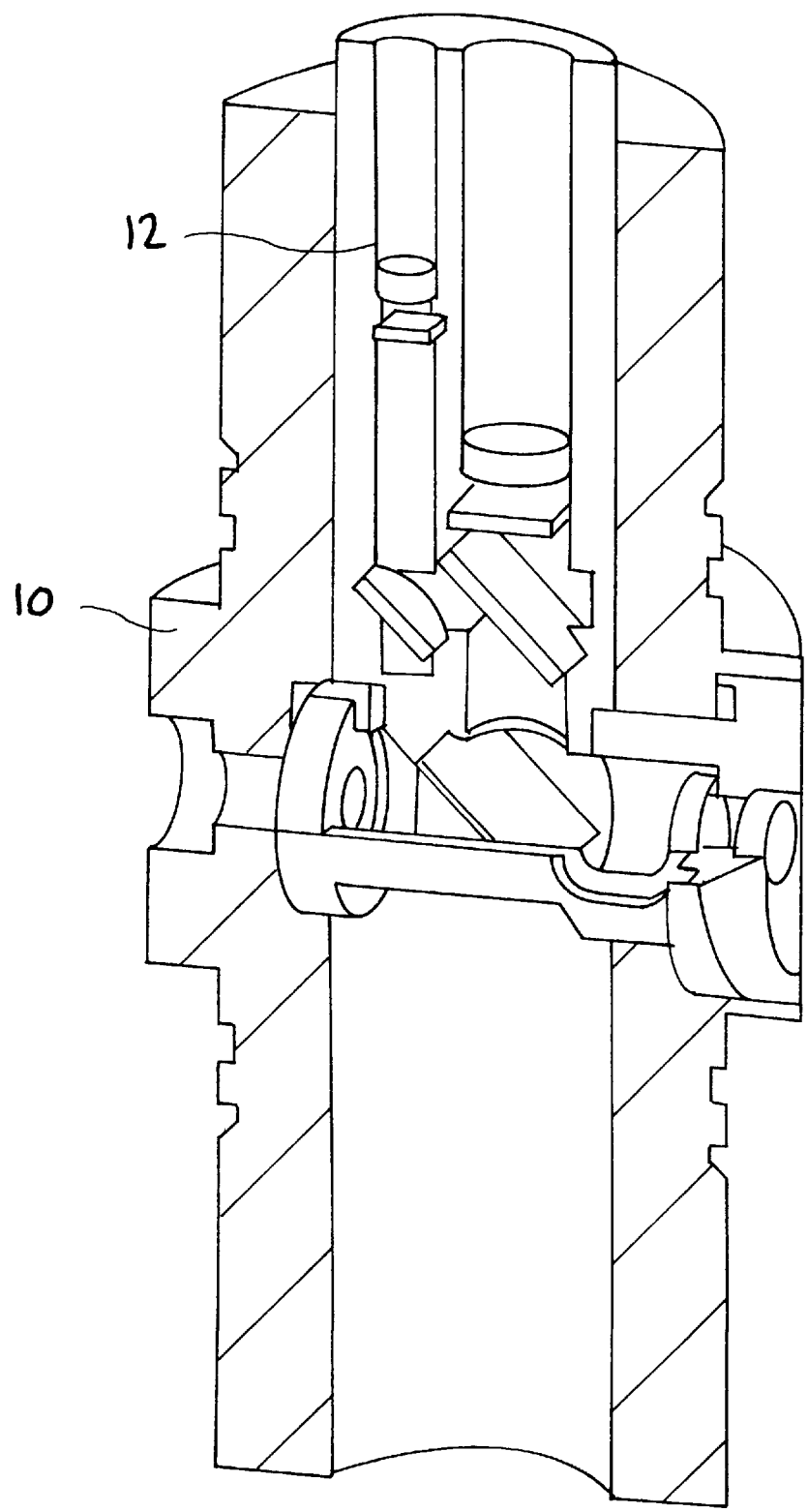
FIG. 1A shows an embodiment of the cone penetrometer fiber optic Raman probe assembly.
Figure 1B:
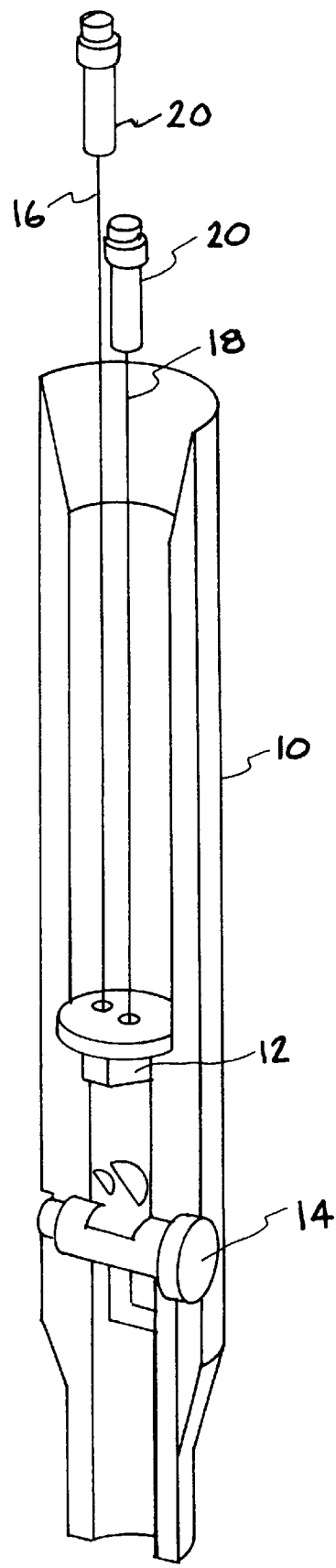
FIG. 1B shows another embodiment of the cone penetrometer fiber optic Raman probe assembly.

Referring to FIG. 1A, the Cone Penetrometer (CPT) Fiber Optic Spectroscopy Probe Assembly consists of two major components, a penetrometer compatible probe housing 10 and an optical Raman probe 12 also referred to as a Raman spectroscopy optical assembly 12. FIG. 1B shows another view of the present invention having a probe housing 10 and a fiber optic Raman probe 12 including a Sapphire window assembly 14. A laser input fiber optic 16 supplies laser light to the fiber optic Raman probe 12, and a signal fiber optic 18 collects light gathered by the fiber optic Raman probe 12. Fiber optics 16 and 18 are terminated with standard connectors 20 such as LEMO OB brand connectors. As shown in FIG. 1B, optical assembly 12 is attached to a flange 13. The flange includes at least one through-hole 11 for a screw. By inserting a screw through the flange and into the uphole lip 15 of probe housing 10, the optical assembly is connected to the probe housing.

Figure 2B:
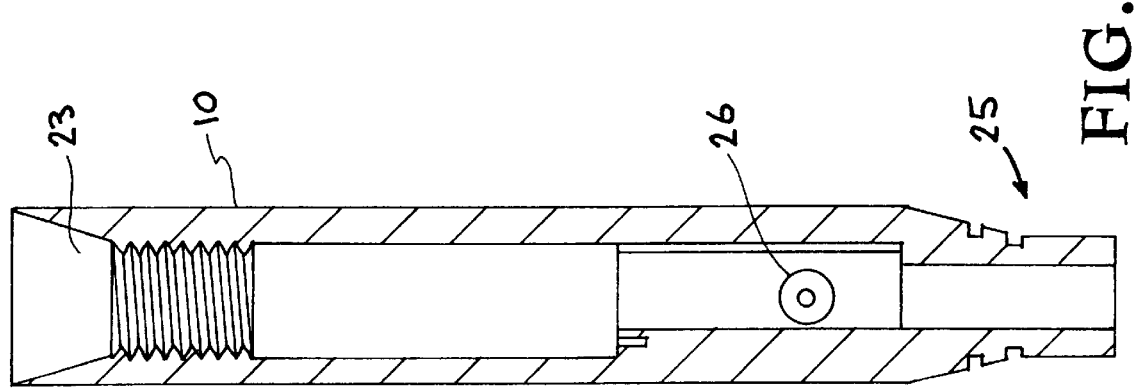
FIG. 2B shows another view of the penetrometer probe main housing.
Figure 2A:
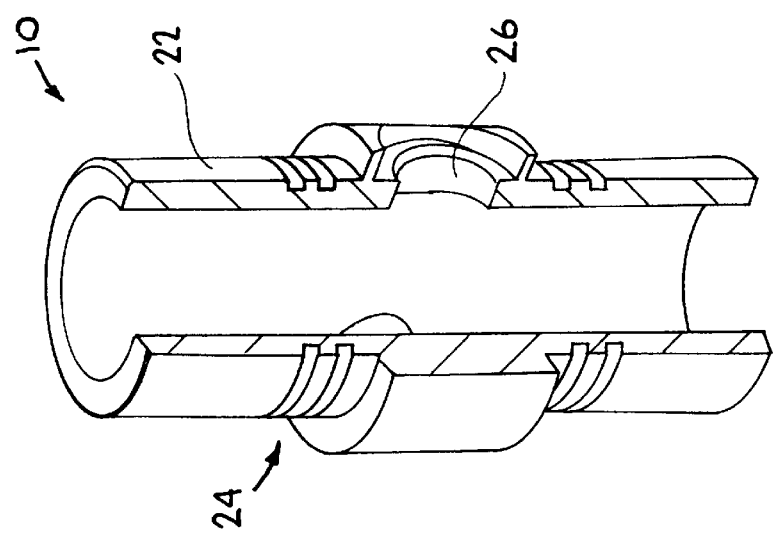
FIG. 2A shows a view the penetrometer probe main housing.

Referring to FIG. 2A, the probe housing 10 includes a thread 22 to enable the housing to be threaded directly into the cone penetrometer push rod (not shown) on the uphole side, and a cone mandrel on the down hole side. O-ring groove 24 is provided. The housing 10 is designed to be an integral unit of the cone penetrometer, supporting a load of a 45 ton vertical push and providing space along its vertical axis for the fiber optic Raman probe 12, and a housing 26 for the window assembly 14 along its radial axis. In one embodiment, a 0.875" diameter circular opening with an inner lip of 0.123" recessed 0.187" from the housing surface provides the mounting base for the window assembly 14. The housing incorporates electrical cable bypasses to allow the passage of wires to electronic sensor packages that may be located in the cone mandrel. FIG. 2B shows a tapered female thread 23, tapered male thread 25 and window housing assembly 26 on probe housing 10. The Probe housing 10 includes an uphole lip 15 and a tapped female thread 21.

Figure 3C:
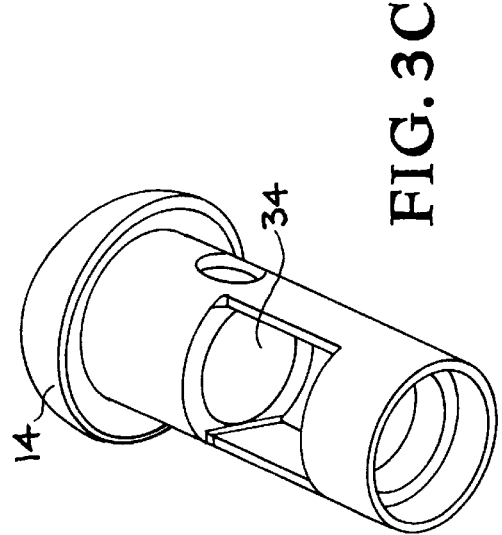
FIG. 3C shows an end view of the window assembly.
Figure 3B:
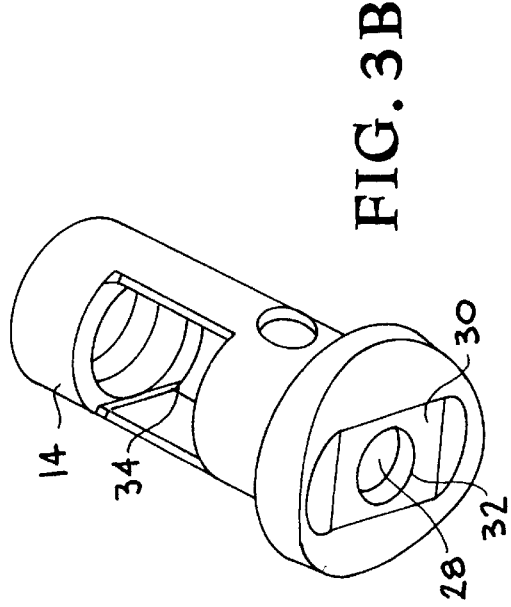
FIG. 3B shows an end view of the window assembly.
Figure 3A:
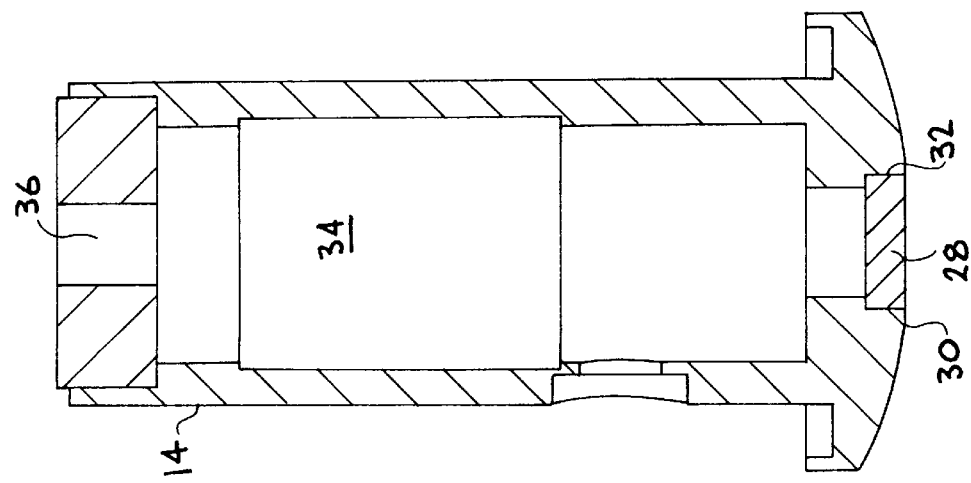
FIG. 3A shows the window assembly of the present invention.

As shown in FIG. 3, the window assembly 14 provides optical communication between the vertically seated Raman probe 12 and the sample environment along the radial axis of the housing 26. Window assembly 14 consists of an insert that mates with the circular opening in the housing. The insert is locked down in the housing with an opposing screw and sealed with o-rings. The window assembly houses a sapphire window 28 which is designed to provide optical access to the sample environment without compromising mechanical strength or chemical resistance. The window 28 is situated in the outer wall of window assembly 14, and is centered about the optical axis of the assembly 14. The dimensions are 6.5 mm in diameter and 2 mm in thickness. The sapphire window 28 resides within a milled flat 30 on the outer surface of the window assembly 14, which provides a surface flush with the window. In one embodiment, the surface tolerance of the window 28 relative to the outer wall of the window assembly is +0.002/−0.000". This tolerance eliminates the possibility of contaminating the external surface of the window with the sample during a push by removing the small dead space allowed by a recessed window. The sapphire window 28, which is edge metallized with a 0.005" layer of Ag, is hermetically sealed directly to the stainless steel body of the window assembly 14 with an indium silver eutectic alloy 32. Sapphire windows have previously been utilized in geological applications of cone penetrometers. An indium silver alloy was selected for its corrosion resistance to sodium nitrate and sodium nitrite in highly alkaline or reactive sample material. The window assembly 14 includes a self-aligning lock-in cavity 34 for the Raman probe 12. The locking feature of lock-in cavity 34 provides self alignment of the optical axis of the probe 12 with the optical axis of the window assembly 14. An embodiment of the window assembly includes a threaded assembly lock-down 36. FIG. 3B shows the sapphire window 28 end of the window assembly. FIG. 3C shows the opposite end facing away from view.

Figure 4:
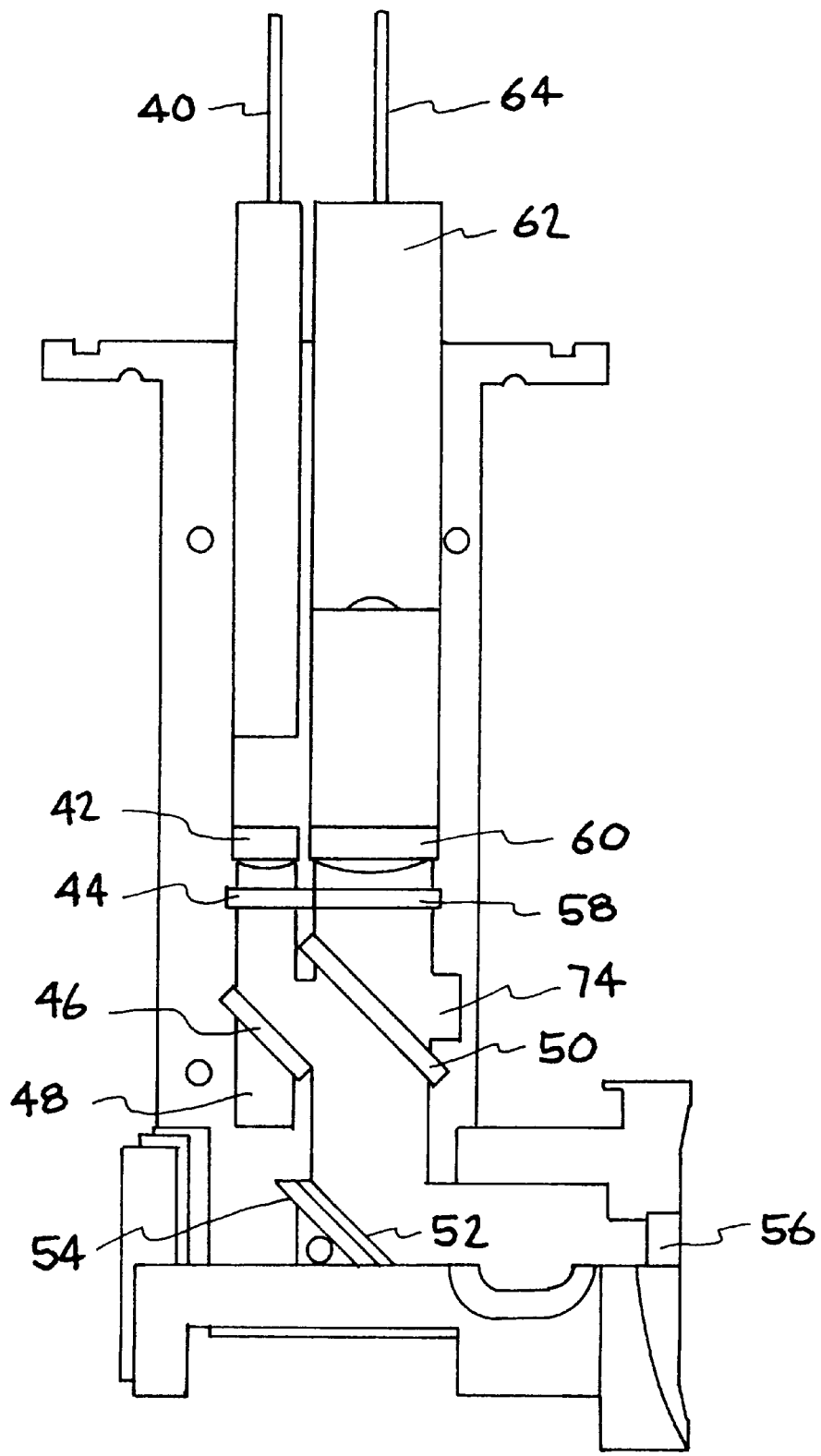
FIG. 4 shows the optical set up of the cone penetrometer fiber optic Raman probe.

Within the probe, the laser input and the Raman signal collection output are divided into two disparate channels (FIG. 4). The following specifications apply to one embodiment. The laser input is introduced into the probe 12 by a 320 $\mu$m optical fiber 40. The f/2.27 output of the laser fiber is collimated with an f/2 lens 42. The collimated laser beam is passed through a dielectric band pass filter 44 to remove silica Raman signal generated in the silica optical fiber between the probe and the laser. The laser beam is then directed 90° into the Raman signal collection channel by dichroic mirror 46. The long pass dichroic mirror acts as a high reflector at the laser wavelength, but transmits residual glass Raman signal into a beam dump within the laser channel. The beam dump 48 acts to reduce the passage of reflected silica Raman signal into the collection channel of the probe. The laser beam is then directed 90° into the signal collection channel by a second dichroic mirror 50, onto a gimbal mounted mirror 52, to exit the Raman probe along the optical axis of the Raman signal collection channel. The screw-driven gimbal mount 54 is used to improve the accuracy and greatly simplify the probe beam alignment. A beam dump 74 associated with dichroic mirror 50 serves as a final silica Raman reduction device. An optional focusing/collimating lens 56 focuses the light from gimbal mounted mirror 52 into the sample area. In the absence of lens 56, a large area is illuminated by the collimated laser light; only collimated signal for this wide area is collected. Raman signal is collected along the same axis, and is collimated by focusing/collimating lens 56. Collimated Raman signal is turned 90° into the Raman signal collection channel by the gimbal mounted mirror 52. Scattered and back reflected laser light is removed from the collected Raman signal by means of the laser turning dichroic filter 50. The scattered and back reflected laser light is reflected back into the laser input channel, while Raman signal passes through the filter 50 along the optical axis of the Raman signal collection channel. Further rejection of scattered laser light is performed by a dielectric long pass filter 58. The collimated Raman signal is focused by an f/2 lens 60 onto a wide diameter optical fiber 62 for transfer to the collection fiber optic bundle 64.

Laser excitation light and Raman signal are conveyed between the optical probe and external laser/analysis systems by means of fiber optic cables. The output of the laser cable 200 $\mu$m fiber is coupled to a 320 $\mu$m fiber, while the input side of a six around one fiber bundle (individual fibers are 200 $\mu$m in core diameter) is coupled to a 800 $\mu$m core fiber. The two fibers (320 and 800 $\mu$m) are connected to the body of the fiber optic probe via steel tubes. The entire probe, consisting of the optical body and transfer fiber optics, is mounted into the CPT Raman probe housing via screws which lock onto the uphole lip of the housing, sealing the space below the flange and mechanically locking the probe in place, as depicted in FIG. 1.

Referring to FIGS. 6A–C, a fiber optic light pipe 66 may be emplaced in a channel 68 inscribed in the signal collection channel of the probe, providing a pathway for illuminating a sample with strobe light from an LED for broadband reflectance measurements. The reflectance data provides sample optical density information that is used to normalize Raman signal intensity for sample absorbance of laser and scattered Raman signal. This feature removes the dependence of returned signal on the color and/or light transmitivity of a sample. Flange 13 and through-holes 11 can be seen in FIGS. 6B and 6C.

Figure 5A:
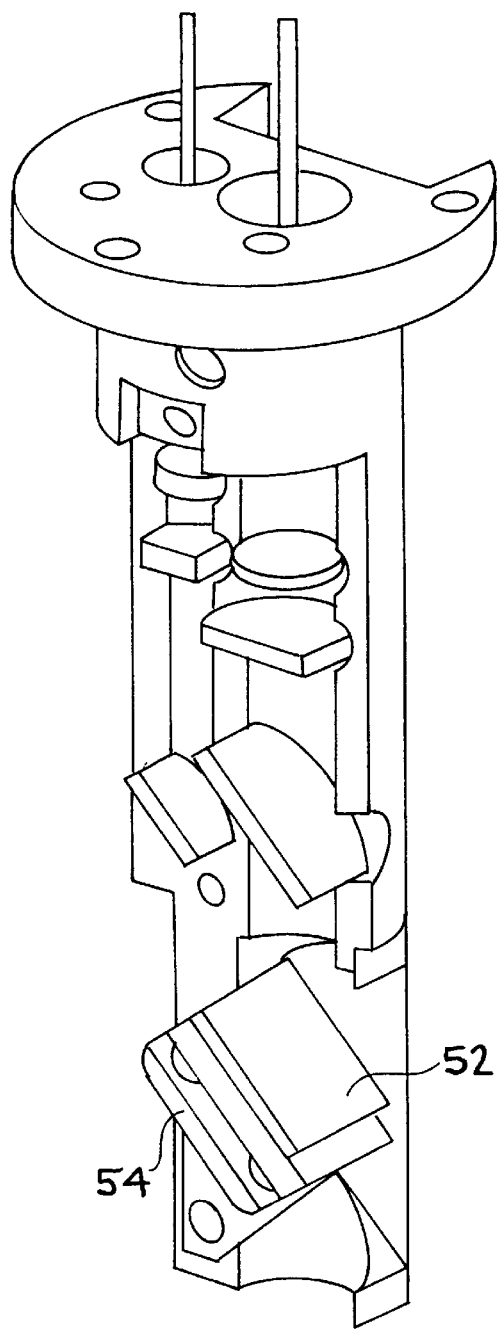
FIG. 5A shows the fiber optic Raman probe in a side viewing configuration.
Figure 5B:
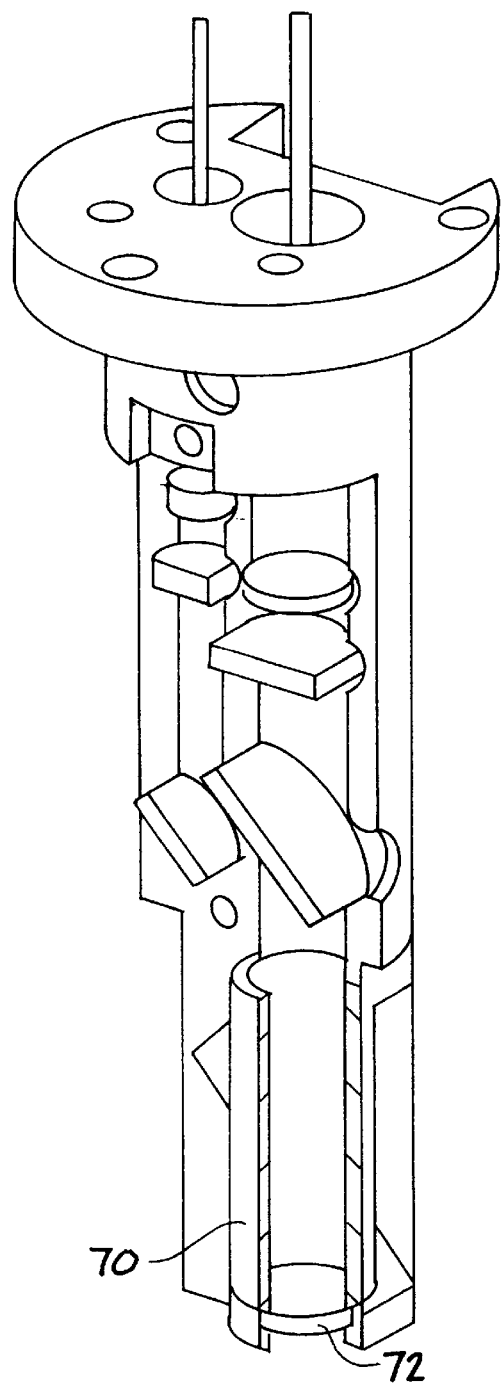
FIG. 5B shows the fiber optic Raman probe in an end viewing configuration.

The gimbal mounted mirror 52 is removable, providing an interchangeable side viewing and end viewing probe configuration. Referring to FIG. 5A, when the gimbal mirror mount 54 is emplaced to turn the beam reflected from the dichroic filter 50 at a 90° angle, the probe is in the side viewing configuration. Referring to FIG. 5B, when the gimbal mirror mount 54 is removed, and an optics tube 70 and optional lens 72 are vertically placed, the probe is then in the end viewing configuration. Flange 13 and through-holes 11 can be seen in FIGS. 5A and 5B.

The outer housing is cone penetrometer compatible and can include either a 1.75 and 2" standard or specialty thread. It is hardened SS for strength and corrosion resistance, compatible with chemically challenging environments, compatible with subsurface environments and has been pushed tested to 45 tons. The window assembly has a hermetically sealed sapphire window which may comprise optical coatings for altering optical characteristics of window. The window assembly includes a corrosion resistant metallic seal, includes means for automatic alignment of the probe to penetrometer window, has focusing and collimating viewing options.

Changes and modifications in the specifically described embodiments can be carried out without departing from the scope of the invention, which is intended to be limited by the scope of the appended claims.

The invention claimed is:

1. A Raman spectroscopy probe for use in a cone penetrometer, comprising:
   a Raman spectroscopy optical assembly comprising first means for sending laser generated light into and receiving Raman light from a test area;
   a housing for said Raman spectroscopy optical assembly; and
   second means for operatively connecting said Raman spectroscopy optical assembly to the inner wall of a cone penetrometer, wherein said second means comprise a flange connected to said optical assembly, wherein said flange includes at least one through-hole, wherein said inner wall of said cone penetrometer includes an uphole lip, wherein said flange is connected to said uphole lip with screws placed through said through-holes of said flange into said uphole lip.

2. The Raman spectroscopy probe of claim 1, wherein said housing comprises hardened stainless steel for strength and corrosion resistance, wherein said housing is compatible with chemically challenging environments.

3. The Raman spectroscopy probe of claim 2, wherein said housing has been pushed tested to at least 45 tons.

4. The Raman spectroscopy probe of claim 3, wherein said Raman spectroscopy optical assembly comprises a window assembly, said window assembly further comprising a hermetically sealed sapphire window.

5. The Raman spectroscopy probe of claim 4, wherein said sapphire window comprises an optical coating.

6. The Raman spectroscopy probe of claim 4, wherein said sapphire window comprises a corrosion resistant metallic seal.

7. The Raman spectroscopy probe of claim 4, wherein said hermetically sealed sapphire window comprises an indium silver eutectic alloy hermetic seal.

8. The Raman spectroscopy probe of claim 1, wherein said Raman spectroscopy optical assembly comprises a window assembly, wherein said window assembly comprises a focusing/collimating lens.

9. The Raman spectroscopy probe of claim 1, wherein said Raman spectroscopy optical assembly comprises removable fiber optics which can be remotely disconnected, wherein said fiber optics are compatible with commercially available fiber connectors.

10. The Raman spectroscopy probe of claim 1, wherein said Raman spectroscopy optical assembly comprises third means for elimination of Raman signal from an input fiber optic.

11. The Raman spectroscopy probe of claim 10, wherein said third means comprise operatively placed dichroic mirrors and beam dumps.

12. The Raman spectroscopy probe of claim 1, wherein said Raman spectroscopy optical assembly comprises a fiber optic collection bundle for increased collection efficiency and a reduced bend radius, wherein said Raman spectroscopy optical assembly is less susceptible to misalignment.

13. The Raman spectroscopy probe of claim 1, wherein said Raman spectroscopy optical assembly comprises a removable gimbal mounted mirror for turning a beam of light from a vertical to radial optical axis to provide interchangeable side and end viewing capability.

14. A Raman spectroscopy probe for use in a cone penetrometer, comprising:
   a Raman spectroscopy optical assembly comprising first means for sending laser generated light into and receiving Raman light from a test area, wherein said Raman spectroscopy optical assembly comprises a window assembly, said window assembly further comprising a hermetically sealed sapphire window;
   a housing for said Raman spectroscopy optical assembly, wherein said housing comprises hardened stainless steel for strength and corrosion resistance, wherein said housing is compatible with chemically challenging environments, wherein said housing has been pushed tested to at least 45 tons; and
   second means for operatively connecting said Raman spectroscopy optical assembly to the inner wall of a cone penetrometer, wherein said first means for sending laser generated light into and receiving Raman light from a test area comprise:
   an optical fiber for providing laser light along a first optical axis;
   a lens for producing collimated light from said laser light;
   a 0° incidence dielectric bandpass filter to remove silica Raman signal from said collimated light to produce a pure laser line;
   a first 45° incidence dielectric long pass filter for reflecting said pure laser line onto a second optical axis that is 90° with respect to said first optical axis, wherein said first 45° incidence dielectric long pass filter transmits any remaining Raman signal;
   a beam dump to receive said remaining Raman signal that is transmitted by said first 45° incidence dielectric long pass filter;
   a second 45° incidence dielectric long pass filter for reflecting light from said second optical axis onto a third optical axis that is 90° with respect to said second optical axis;
   a second beam dump to receive said remaining Raman signal that is transmitted by said second 45° incidence dielectric long pass filter;
   a gimbal mounted mirror for reflecting light from said third optical axis onto a fourth optical axis that is 90° with respect to said third optical axis;
   wherein said sapphire window has an inner surface that is facing said gimbal mounted mirror,
   wherein light propagating on said fourth optical axis passes through said sapphire window and further propagates as test light into a test environment, wherein said test light interacts with said test environment to produce said Raman light, wherein some of said signal light is collected through said sapphire window and propagates along said fourth optical axis, is reflected by said gimbal mounted mirror onto said third optical axis and is transmitted through said second 45° incidence dielectric long pass filter to produce collected signal light;
   a 0° incidence dielectric long pass filter for rejection of scattered laser light propagating with said collected signal light to produce pure signal light;
   a second lens for focusing said pure signal light to produce focused pure signal light; and
   a fiber optic bundle for collecting said focused pure signal light.

15. The Raman spectroscopy probe of claim 14, further comprising an optional focusing/collimating lens located between said gimbal mounted mirror and said inner surface of said sapphire window.

16. A Raman spectroscopy probe for use in a cone penetrometer, comprising:
   a Raman spectroscopy optical assembly comprising first means for sending laser generated light into and receiving Raman light from a test area, wherein said Raman spectroscopy optical assembly comprises a window assembly, said window assembly further comprising a hermetically sealed sapphire window;

a housing for said Raman spectroscopy optical assembly, wherein said housing comprises hardened stainless steel for strength and corrosion resistance, wherein said housing is compatible with chemically challenging environments, wherein said housing has been pushed tested to at least 45 tons; and second means for operatively connecting said Raman spectroscopy optical assembly to the inner wall of a cone penetrometer, wherein said first means for sending laser generated light into and receiving Raman light from a test area comprise:

an optical fiber for providing laser light along a first optical axis;

a lens for producing collimated light from said laser light;

a 0° incidence dielectric bandpass filter to remove silica Raman signal from said collimated light to produce a pure laser line;

a first 45° incidence dielectric long pass filter for reflecting said pure laser line onto a second optical axis that is 90° with respect to said first optical axis, wherein said first 45° incidence dielectric long pass filter transmits any remaining Raman signal;

a beam stop to receive said remaining Raman signal that is transmitted by said first 45° incidence dielectric long pass filter;

a second 45° incidence dielectric long pass filter for reflecting light from said second optical axis onto a third optical axis that is 90° with respect to said second optical axis;

a second beam dump to receive said remaining Raman signal that is transmitted by said second 45° incidence dielectric long pass filter;

wherein light propagating on said third optical axis propagates through said sapphire window as test light into a test environment, wherein said test light interacts with said test environment to produce said Raman light, wherein some of said signal light is collected through said sapphire window and propagates along said third optical axis, is transmitted through said second 45° incidence dielectric long pass filter to produce collected signal light;

a 0° incidence dielectric long pass filter for rejection of scattered light propagating with said collected signal light to produce pure signal light;

a second lens for focusing said pure signal light to produce focused pure signal light; and a fiber optic bundle for collecting said focused pure signal light.

17. The Raman spectroscopy probe of claim 16, further comprising an optional focusing/collimating lens located between said second 45° incidence dielectric long pass filter and said sapphire window.

* * * * *